US005221668A

United States Patent [19]

Henningfield et al.

[11] Patent Number: 5,221,668

[45] Date of Patent: Jun. 22, 1993

[54] NUTRITIONAL PRODUCT FOR TRAUMA AND SURGERY PATIENTS

[75] Inventors: Mary F. Henningfield, Columbus; John W. McEwen, Hilliard; Robert H. Miller, Worthington, all of Ohio

[73] Assignee: Abbott Laboratories, Abbott Park, Ill.

[21] Appl. No.: 840,972

[22] Filed: Feb. 26, 1992

[51] Int. Cl.⁵ .................... A61K 31/195; A61K 37/02
[52] U.S. Cl. ........................ 514/23; 424/439; 424/442; 426/601; 426/606; 426/607; 426/656; 426/658; 426/800; 426/801; 426/810; 514/2; 514/878; 514/909; 514/911; 514/921
[58] Field of Search .............. 514/2, 23, 878, 909, 514/911, 921; 424/439, 442; 426/601, 606, 607, 656, 658, 800, 801, 810

[56] References Cited

U.S. PATENT DOCUMENTS

| | | | |
|---|---|---|---|
| 4,042,688 | 8/1977 | Gans et al. | 514/21 |
| 4,438,144 | 3/1984 | Blackburn | 514/885 |
| 4,850,704 | 7/1989 | Zimmerly et al. | 366/263 |
| 4,920,098 | 4/1990 | Cotter et al. | 514/2 |
| 5,053,387 | 10/1991 | Alexander | 514/2 |
| 5,085,883 | 2/1992 | Garleb et al. | 426/590 |

FOREIGN PATENT DOCUMENTS

| | | |
|---|---|---|
| 3691784 | 12/1984 | Australia . |
| 0312612 | 4/1989 | European Pat. Off. . |
| 0362724 | 5/1990 | European Pat. Off. . |
| 61-192245 | 8/1986 | Japan . |
| 9109524 | 7/1991 | PCT Int'l Appl. . |

OTHER PUBLICATIONS

Sales Literature for IMPACT ®, published by Sandoz Nutrition, © 1990.
Sales Literature for IMMUM-AID ™, published by McGaw, Inc., not dated.
Sales Literature for OSMOLITE ® HN, published by Ross Laboratories, 1986.

Primary Examiner—Ronald W. Griffin
Attorney, Agent, or Firm—Lonnie R. Drayer; Donald O. Nickey

[57] ABSTRACT

A liquid nutritional product for trauma and surgery patients has a caloric density of about 1.2 to 1.5 Kcal/mL and a calorie to nitrogen ratio of about 112:1 to 145:1. A portion of the protein system comprises partially digested protein, and supplemental L-arginine provides about 1-3% of the total calories in the product. The lipid system has a ratio of linoleic acid to alpha linoleic acid in the range of about 3.5:1 to about 5.5:1.

26 Claims, No Drawings

NUTRITIONAL PRODUCT FOR TRAUMA AND SURGERY PATIENTS

FIELD OF THE INVENTION

The present invention relates to a nutritional product for persons subjected to trauma or surgery.

BACKGROUND OF THE INVENTION

Trauma is a leading health problem in the United States today. Trauma is the number one killer of young adults and it ranks third overall, following heart disease and cancer. For every American who dies as a result of trauma, there are three Americans permanently disabled (500,000 permanent disabilities/year).

Approximately 50% of deaths from trauma occur within seconds of the injury. Trauma prevention is the only way to alter deaths which occur immediately following injury. A second peak in deaths occurs within two or three hours after the trauma and is dependent upon available intervention and treatment of the life-threatening aspects of the injury. The third peak occurs days or even weeks following the injury and is usually caused by sepsis and/or multiple organ failure. Sepsis may be defined as the presence of bacterial infection. Septicemia continues to be a problem in the critically ill, surgical or traumatized patient. Death secondary to systemic sepsis is not uncommon and may occur two to four weeks after the initial injury.

Severe injury or trauma, including surgery, is associated with loss of the body's nutrient stores due both to the injury itself and the resulting catabolic state. For optimal recovery, critically ill patients need proper nutritional intake. Lack of it can result in malnutrition-associated complications, including prolonged negative nitrogen balance, depletion of somatic and visceral protein levels, immune incompetence, increased risk of infection, and other complications associated with morbidity and mortality. A primary objective of nutritional support for the traumatized person is to replace or maintain the body's normal level of nutrients by providing adequate energy substrates, protein, and other nutrients essential for tissue repair and recovery.

While nutrients may be provided by either parenteral or enteral routes, clinicians are making greater efforts to use the enteral route in light of research showing that enteral feeding confers certain physiologic benefits not seen with parenteral feeding. Published studies have reported that early enteral feeding provides energy and nutrients essential for optimal healing and immunocompetence, helps maintain the gut mucosal integrity, and may blunt catabolic effects and normalize blood glucose levels. Certain nutrients have effects on the gastrointestinal tract and immune system that go beyond the provision of nutrition. For example, beta-carotene, lactalbumin, and arginine are known to have specific physiologic benefits that are especially important for trauma and surgical patients.

Severe injury and major surgery causes abrupt changes in body metabolism. These changes vary with the type of trauma, previous health status, and medical care. Hormonally mediated hypermetabolism, catabolism, elevated basal metabolic rate and nitrogen excretion, altered fluid and electrolyte balance, synthesis of acute phase proteins, inflammation, and immunosuppression are often observed after severe injury, major surgery, or critical illness. The gastrointestinal tract is frequently affected by trauma or surgery. Blood flow may be reduced by hemorrhage, and the resulting loss of oxygen and nutrients may damage mucosal cells. However, the presence of intraluminal nutrients helps protect the gastrointestinal tract.

Epithelial cells such as those lining the gut are an important barrier against bacterial infection. The importance of the "first line of defense" provided by epithelial cells is evident, for example, in the patient suffering from a serious burn who is at risk of infection due to the destruction of skin.

Appropriate enteral nutrition following injury may minimize malnutrition, provide nutrients to the immune system and maintain the gut epithelial which acts as a barrier to translocation of bacteria. This may help prevent the development of sepsis. Malnutrition may compromise the immune system and contribute to the high incidence of septic complications. It has been reported that cell-mediated immunity is reduced in proportion to the level of malnutrition of the critically ill patient.

Following severe trauma and major surgery, gastrointestinal disturbances such as diarrhea, abdominal bloating and aspiration, have been associated with enteral feeding. These disturbances are caused by complex interactions between the trauma response, antibiotic and drug therapy as well as the enteral feeding. If at all possible, enteral feeding is advised to maintain mucosal integrity. The well-known "paralytic ileus" is usually confined to the stomach. The small intestine may retain motility and often enteral nutritional through the small intestine can be used successfully. It is essential that the proper administration of nutrients, including water, be monitored in order to prevent a further deterioration of the nutrient status of the critically ill patient. For those patients who are volume intolerant it is difficult to meet their caloric requirements with standard enteral nutritional products.

Both anabolic and catabolic processes are accelerated following severe trauma, although catabolism predominates. This response allows muscle breakdown to occur in order to provide amino acids for synthesis of proteins involved in immunological response and tissue repair. However, some mobilization of protein and calcium can be attributed to bed rest. Disuse atrophy contributes to the muscle wasting and negative nitrogen balance frequently observed in the trauma patient.

The catabolism of trauma occurs as a mechanism to provide substrate through the breakdown of muscle tissue. Hypermetabolism also occurs; however, it is difficult to meet the caloric needs of the patient. Dietary protein may be utilized as an energy substrate which necessitates the excretion of nitrogenous products. Catabolism following trauma or major surgery may be obligatory and it is uncertain whether it could be altered by the intake of large doses of protein. Overall negative nitrogen balance observed in traumatized and septic patients may be attributed to an inadequate caloric intake, rather than an insufficient protein intake.

The nutritional support of trauma and surgery patients has been extensively investigated in the prior art.

There are commercially available nutritional products intended for trauma or surgery patients. IMPACT ® is a ready-to-use enteral formula which is distributed by SANDOZ NUTRITION, Minneapolis, Minn., U.S.A.. IMPACT ® contains a much greater level of L-arginine than the product of the present invention, and has a lower caloric density than the product of the present invention. IMMUN-AID ™, a nutritional product for immunocompromised patients, is distributed by McGaw, Inc. of Irvine, Calif., U.S.A.. IMMUN-AID TM is distributed in powdered form and contains intact protein and amino acids. OSMOLITE ® HN distributed by Ross Laboratories of Columbus, Ohio, U.S.A. is not specifically formulated for trauma or surgery patients but has often been employed for this purpose.

U.S. Pat. No. 4,042,688 relates to a nutritional supplement, taken for example in tablet form, which contains predigested protein in the form of a gelatin hydrolysate. The gelatin hydrolysate used in that invention is made by hydrolyzing animal collagen, preferably a collagen derived from the skin of pork bellies, by means of enzymatic hydrolysis, and then spray drying the gelating solution. The predigested protein employed in the present invention is a higher quality protein than that derived from gelatin, and the nutritional product of the present invention provides a balanced diet rather than being a diet supplement.

U.S. Pat. No. 4,438,144 teaches a nutritional composition that may be provided either enterally or parenterally, preferably parenterally, wherein the amino acids comprise from about 70 to 100% valine, isoleucine and leucine, collectively. However, the nutritional product of the present invention is formulated to provide a balanced diet and does not contain such high concentrations of these specific amino acids.

U.S. Pat. No. 4,920,098 relates to a method of providing nutritional support as cardiac therapy. This therapy regimen may be administered either parenterally or enterally. The nutritional product is formulated to provide energy and protein substrates that are especially beneficial to cardiac tissues. Although the caloric distribution taught in this patent is similar to that of the nutritional product disclosed herein, the new product contains a much different protein system and is formulated for a different patient population.

U.S. Pat. No. 5,053,387 teaches a nutritional composition containing intact protein, preferably whey, and contains arginine in the amount of about 1-3% of the total energy intake. In a preferred embodiment the lipid consists of a mixture of equal amounts of fish oil and safflower oil. The caloric distribution of the composition taught in this patent is substantially different from that of the nutritional product of the present invention.

Published Australian Patent Application 36917/84 relates to an amino acid solution that may be provided either enterally or parenterally to a patient, but does not teach a composition for providing a balanced diet as in the present invention.

Published European Patent Application No. 0 367 724 teaches a nutritional composition containing intact protein, arginine and marine oil. It has a caloric density which is substantially lower than that of the nutritional product of the present invention.

Published PCT application WO 91/09524 relates to a method of treating a patient having an impaired immune response due to trauma or surgery. The method involves providing the patient with about 15 to 35 grams of arginine per day. Nutritional formulations for providing the arginine are disclosed in this PCT application. Arginine is provided at a level of about 6.9 to 11.1 grams per 1,500 kcal by the nutritional product of the present invention (with 1,5000 kcal per day being the nutrient base of the new product).

European Patent Application 0 312 612 teaches a "nutritive emulsion" containing an "amino acid preparation", a lipid and water. The caloric density of the "nutritive emulsion" is adjusted to a desired level by the amount of sugar in the emulsion.

Japanese Patent Application Sho 61-192245 teaches that cows milk protein should be supplemented by arginino at a level of 3.5-7.0% of the amino acids in the product for a nutritional product for infants. The nutritional product of the present invention has an amino acid profile containing 9.0 to 13.8% arginine.

DETAILED DESCRIPTION OF THE INVENTION

Table 1 presents the bill of materials for manufacturing 60,000 pounds of a liquid nutritional product according to the present invention.

TABLE I

| INGREDIENT | QUANTITY PER 60,000 LBS. OF PRODUCT |
|---|---|
| WATER | 42481.22 lbs |
| HYDROLYZED CORNSTARCH | 10517.95 lbs |
| PARTIALLY HYDROLYZED SODIUM CASEINATE | 2642.06 lbs |
| LACTALBUMIN HYDROLYSATE | 1093.71 lbs |
| CANOLA OIL | 837.60 lbs |
| MEDIUM-CHAIN TRIGLYCERIDES (FRACTIONATED COCONUT OIL) | 837.60 lbs |
| L-ARGININE | 374.40 lbs |
| CORN OIL | 335.04 lbs |
| MAGNESIUM CHLORIDE | 152.47 lbs |
| POTASSIUM CITRATE | 152.12 lbs |
| CALCIUM PHOSPHATE TRIBASIC (PREFERABLY MICRONIZED) | 148.15 lbs |
| CITRIC ACID | 124.22 lbs |
| SOY LECITHIN | 83.76 lbs |
| ASCORBIC ACID | 38.36 lbs |
| POTASSIUM PHOSPHATE DIBASIC | 37.70 lbs |
| CHOLINE CHLORIDE | 33.53 lbs |
| IOTA CARRAGEENAN | 25.50 lbs |
| 45% POTASSIUM HYDROXIDE | 25.26 lbs |
| POTASSIUM CHLORIDE | 14.62 lbs |
| ULTRATRACE/TRACE MINERAL PREMIX | 14.41 lbs |
| ZINC SULFATE | 1338.91 gms |
| FERROUS SULFATE | 1287.79 gms |
| MANGANESE SULFATE | 353.72 gms |
| CUPRIC SULFATE | 190.75 gms |
| SODIUM MOLYBDATE | 9.64 gms |
| CHROMIUM CHLORIDE | 9.38 gms |
| SODIUM SELENITE | 3.65 gms |
| CITRIC ACID | 403.46 gms |

TABLE I-continued

| INGREDIENT | QUANTITY PER 60,000 LBS. OF PRODUCT |
|---|---|
| SUCROSE (Carrier) | 2939.70 gms |
| TAURINE | 11.24 lbs |
| L-CARNITINE | 9.26 lbs |
| WATER SOLUBLE VITAMIN PREMIX | 2100.00 gms |
| NIACINAMIDE | 788.01 gms |
| CALCIUM PANTOTHENATE | 509.71 gms |
| THIAMINE CHLORIDE HYDROCHLORIDE | 130.10 gms |
| PYRIDOXINE HYDROCHLORIDE | 125.24 gms |
| RIBOFLAVIN | 101.67 gms |
| FOLIC ACID | 17.65 gms |
| BIOTIN | 15.34 gms |
| CYANOCOBALAMIN | 0.35 gms |
| DEXTROSE (Carrier) | 411.93 gms |
| OIL SOLUBLE VITAMIN PREMIX | 1500.00 gms |
| ALPHA-TOCOPHERYL ACETATE | 1209.00 gms |
| PHYLLOQUINONE | 2.10 gms |
| VITAMIN D3 | 0.27 gms |
| COCONUT OIL (carrier) | 288.63 gms |
| 30% BETA-CAROTENE | 747.69 gms |
| VITAMIN A PALMITATE | 100.60 gms |
| POTASSIUM IODIDE | 4.20 gms |
| 2.5% VITAMIN D3 | 1.76 gms |

The liquid nutritional product of the present invention is manufactured by preparing three slurries which are then blended together, heat treated, standardized, packaged and sterilized. The process for manufacturing 60,000 pounds of the liquid nutritional product, using the bill of materials from Table 1, is described in detail below.

A carbohydrate/mineral slurry is prepared by first heating about 9,600 pounds of water to a temperature in the range of about 155° to 165° F. with agitation. The ultratrace/trace mineral premix is added to the water and dissolved by agitating the resultant solution for at least one minute. The following minerals are then added, in the order listed, with high agitation:

Potassium Iodide
Potassium Citrate
Magnesium Chloride
Potassium Chloride
Potassium Phosphate Dibasic
Calcium Phosphate Tribasic The hydrolyzed cornstarch is then added to the resultant slurry. The completed carbohydrate/mineral slurry is held with high agitation at a temperature in the range of about 155° F. to 165° F. for not longer than 12 hours until it is blended with the other slurries.

A protein-in-fat slurry is prepared by combining and heating the Medium Chain Triglycerides (fractionated coconut oil), corn oil and canola oil to a temperature in the range of about 90° F. to 110° F. with agitation. The oil soluble vitamin premix, 2.5% vitamin D3, vitamin A palmitate, and 30% beta carotene are added to the slurry with agitation. The soy lecithin and carrageenan are then added to the slurry with agitation. (While iota-carrageenan is believed to be best when the product is to be packaged in metal cans and terminally sterilized, it is within the scope of the invention to use other forms of carrageenan if other packaging or sterilizing systems are used.) 40% of the partially hydrolyzed sodium caseinate is then added to the slurry with agitation. The completed protein-in-fat slurry is held under moderate agitation at a temperature in the range of about 90° F. to 110° F. for not longer than 12 hours until it is blended with the other slurries.

A protein-in-water slurry is prepared by first heating about 25,200 pounds, (½ of the total water in each of two separate vessels), of water to a temperature in the range of about 130° F. to 150° F. with agitation. The slurry is maintained at a temperature in this range throughout the process of preparing the slurry. The L-arginine and citric acid are dumped directly into about half of the water with agitation, then the remaining water is added to the resultant solution remaining 60% of the partially hydrolyzed sodium caseinate is blended into the L-arginine/citric acid solution using a mixing apparatus such as the two stage blender which is described in U.S. Pat. No. 4,850,704, which is incorporated herein by reference for the purpose of teaching appropriate equipment for practicing the present invention. The lactalbumin hydrolysate is added to the slurry using the above described mixing apparatus. It was discovered that adding the L-arginine and citric acid to water via the mixing apparatus of U.S. Pat. No. 4,850,704 may cause manufacturing problems. The completed protein-in-water slurry is held under agitation at a temperature in the range of about 130° to 150° F. for not longer than 2 hours before being blended with the other slurries. In large scale production it is desirable to prepare the protein-in-water slurry in several smaller batches to minimze the probability of microbial contamination of the slurry if it sits too long before being blended with the other slurries.

The protein-in-fat and protein-in-water slurries are blended together with agitation and the resultant blended slurry is maintained at a temperature in the range of about 130° F. to 150° F. After waiting at least one minute the carbohydrate/mineral slurry is added to the blended slurry from the preceding step with agitation and the resultant blended slurry is maintained at a temperature in the range of about 130° F. to 150° F. The vessel which contained the carbohydrate/mineral slurry should be rinsed with about 50 gallons of water and the rinse water should be added to the blended slurry.

After waiting a period of not less than one minute nor greater than two hours the blended slurry is subjected to deaeration, Ultra-High-Temperature (UHT) treatment, and homogenization, as described below.

A. Use a positive pump for supplying the blended slurry for this procedure.

B. Heat the blended to a temperature in the range of about 150° F. to 160° F. slurry by passing it through a heat exchanger.
C. Deaerate the blended slurry to 10-15 inches Hg.
D. Emulsify the blended slurry at 900-1,100 psi.
E. Heat the blended slurry to a temperature in the range of about 248° F. to 252° F. by passing it through a plate/coil heater with a hold time of approximately 10 seconds.
F. UHT heat the blended slurry to a temperature in the range of about 292° F. to 296° F. with a hold time of approximately 5 seconds.
G. Reduce the temperature of the blended slurry to be in the range of about 248° F. to 252° F. by passing it through a flash cooler.
H. Reduce the temperature of the blended slurry to be in the range of about 165° F. to 185° F. by passing it through a plate/coil cooler.
I. Homogenize the blended slurry at about 3,900 to 4,100 psi.
J. Pass the blended slurry through a hold tube for at least 16 seconds at a temperature in the range of about 165° F. to 185° F.
K. Cool the blended slurry to a temperature in the range of about 34° F. to 44° F. by passing it through a large heat exchanger.
L. Store the blended slurry at a temperature in the range of about 34° F. to 44° F., preferably with agitation.

Two vitamin solutions are prepared separately and then added to the blended slurry. The first vitamin solution is prepared by heating 90 gallons of water to a temperature in the range of about 110° F. to 150° F. with agitation, and thereafter adding the taurine and water soluble vitamin premix to the water. The second vitamin solution is prepared by providing 90 gallons of room temperature water and adding the choline chloride, ascorbic acid, L-carnitine and 25.26 pounds of 45% potassium hydroxide to the water with agitation. The two vitamin solutions are then added to the blended slurry with agitation within one hour after the vitamin solutions are prepared. If necessary, diluted potassium hydroxide is added to the blended slurry such that the product will have a pH in the range of 6.4 to 7.0 after sterilization. The completed product is then placed in suitable containers and subjected to sterilization.

The nutritional profile of the liquid nutritional product of the present invention is presented in Table 2.

TABLE 2

| NUTRIENT | Amt/1500 kcals | % U.S. RDA/ 1500 kcals | Amt/8 oz | % U.S. RDA/ 8 oz | Amount/L |
|---|---|---|---|---|---|
| Protein, g | 76.9 | *** | 15.8 | *** | 66.6 |
| Fat, g | 43.1 | *** | 8.8 | 888 | 37.4 |
| Carbohydrate, g | 204.4 | *** | 42.0 | *** | 177.2 |
| Water, g | 910 | *** | 187 | *** | 789 |
| Vitamin A Activity, IU[1] | 10,000 | 200% | 2053 | 41.1% | 8666 |
| I Vitamin D, IU | 400 | 100% | 83 | 20.8% | 347 |
| I Vitamin E, IU | 45 | 150% | 9.3 | 31% | 39 |
| Vitamin K, mcg | 80 | *** | 17 | *** | 70 |
| Vitamin C, mg | 300 | 500% | 62 | 103% | 260 |
| Folic Acid, mcg | 600 | 150% | 124 | 31% | 520 |
| Thiamin | 2.3 | 150% | 0.48 | 32% | 2.0 |
| Riboflavin, mg | 2.55 | 150% | 0.53 | 31.2% | 2.3 |
| Vitamin B-6, mg | 3.0 | 150% | 0.62 | 31% | 2.6 |
| Vitamin B-12, mcg | 9.0 | 150% | 1.9 | 31.7% | 7.8 |
| Niacin, mg | 30 | 150% | 6.2 | 31% | 26 |
| Choline, mg | 600 | *** | 124 | *** | 520 |
| Biotin, mcg | 450 | 150% | 93 | 31% | 390 |
| Pantothenic acid, mg | 15 | 150% | 3.08 | 30.8% | 13 |
| Sodium, mg | 1200 | *** | 250 | *** | 1040 |
| Potassium, mg | 2000 | *** | 410 | *** | 1730 |
| Chloride, mg | 1900 | *** | 390 | *** | 1650 |
| Calcium, mg | 1000 | 100% | 206 | 20.6% | 867 |
| Phosphorous, mg | 1000 | 100% | 206 | 20.6% | 867 |
| Magnesium, mg | 400 | 100% | 82.2 | 20.6% | 347 |
| Iodine, mcg | 150 | 100% | 30.8 | 20.5% | 130 |
| Manganese, mg | 5 | *** | 1.03 | *** | 4.34 |
| Copper, mg | 2 | 100% | 0.42 | 21% | 1.74 |
| Zinc, mg | 22.5 | 150% | 4.62 | 30.8% | 19.5 |
| Iron, mg | 18 | 100% | 3.70 | 20.6% | 15.6 |
| Selenium, mcg | 70 | *** | 15 | *** | 61 |
| Chromium, mcg | 100 | *** | 21 | *** | 87 |
| Molybdenum, mcg | 150 | *** | 31 | *** | 130 |
| L-Carnitine, mg | 150 | *** | 31 | *** | 130 |
| Taurine, mg | 150 | *** | 31 | *** | 130 |

*** USRDA not established.
[1] Includes Vitamin A activity from beta-carotene and vitamin A palmitate.

The body's stores of protein are in a constant state of breakdown and synthesis. Tissues differ in their rate of protein turnover, from rapid (intestinal mucosal cells) to relatively slow (muscle). The daily amount of protein turnover far exceeds dietary intake, indicating a great conservation of amino acids. However, many metabolic nitrogenous products, such as urea, are lost daily. These losses contribute to a need for nitrogen in the form of dispensable (nonessential) amino acids in addition to the need for indispensable (essential) amino acids for protein components of tissues.

Dietary proteins that provide a balanced amino acid profile and are biologically available are referred to as high-quality proteins. Protein requirements cannot be totally separated from energy requirements because protein is used as an energy substrate and not for tissue synthesis in the absence of adequate calories.

That protein deficiency rarely occurs independent of calorie malnutrition demonstrates the interrelationship of protein and energy needs. Protein deficiency is usually exhibited in the form of protein energy malnutrition. Both anabolic and catabolic processes are accelerated after severe trauma, although catabolism predominates. Accelerated catabolism after trauma provides substrate through the breakdown of muscle tissue. This mechanism provides amino acids for synthesis of proteins involved in immunologic response and tissue repair. The hypermetabolism that occurs after injury often makes meeting the patient's caloric needs difficult. In the nutritional product of the present invention the caloric density is about 1.2 to 1.5 kcal/ml, preferably about 1.3 kcal/mL and the total calorie to nitrogen ratio is about 112:1 to about 145:1, most preferably about 115:1 to about 135:1. The advantage of this caloric density is that a smaller volume of the product is required to meet the patient's needs, and many trauma or surgical patients have restricted fluid intakes and/or volume intolerant. Volume intolerance is not uncommon, for example, young adult males have normally high metabolic rates which may be accelerated even further by trauma so that a large number of calories are required daily. If the caloric density (kcal/ml) is too low the volume of product required may result in bloating and/or difficulty feeding a sufficient volume through a feeding tube. One of the problems solved by the nutritional product of the present invention is not simply providing a particular caloric density, but a particular caloric density in which about 18-24%, most preferably about 20.5% of the calories are provided by proteins; about 20-30%, preferably about 23-27% and most preferably about 24-26% of the calories are provided by lipids; and about 46 to 62%, preferably 50-58%, most preferably about 52-56% of the calories are provided by carbohydrates. Current U.S. guidelines for healthy persons state that about 15% of calories should be contributed by protein, less than 30% from fat and the remainder by carbohydrate. The nutritional invention provides a higher level of a protein and the protein is from a blend which provides a balanced amino acid profile. The protein level is not as high as some commercial formulas so as to avoid potential problems.

When protein supplies energy, only the carbon skeleton of the constituent amino acids are used, whereas the nitrogen is excreted through the urine. The negative nitrogen balance observed in critically ill patients may be attributed to an inadequate caloric intake, rather than an insufficient protein intake. Accelerated catabolism and large urinary nitrogen losses after trauma may be obligatory. It is uncertain whether providing large amounts of protein can alter catabolism or nitrogen losses after injury or illness. In addition, some mobilization of protein and calcium results from bed rest. Disuse atrophy contributes to the muscle wasting and negative nitrogen balance frequently observed in the immobilized trauma patient.

In the nutritional product of the invention the protein system comprises lactalbumin hydrolysate, partially hydrolyzed sodium caseinate and L-arginine. The (AOAC) Association of Official Analytical Chemists protein efficiency ratio assays of the nutritional product of the present invention indicated that the product has good quality protein. About 20-35%, preferably about 20-30% and most preferably about 22-27% by weight of the protein system comprises lactalbumin hydrolysate (a suitable commercially available commodity is Alatal TM 817 which is distributed by New Zealand Milk Products); about 60-70%, preferably about 62-68% and most preferably about 64-66% by weight of the protein system comprises partially hydrolyzed sodium caseinate; (a suitable commercially available commodity is Alanate TM 166 which is distributed by New Zealand Milk Products; and about 8-14%, preferably about 8-12%, and most preferably about 9-11% by weight of the protein system comprises L-arginine. Preferably the L-arginine is not in the form of arginine HCL or a DL-arginine mix because only the L-arginine provides the desired effect on the patient. A liquid nutritional product according to the present invention provides about 6.9-11.1 grams of arginine per 1,500 kcal, with 1,500 kcal being the nutrient base provided to the average patient in a 24 hour period. It is further considered to be critical to the practice of the invention that the supplemental L-arginine (excluding the L-arginine that may be inherent in other ingredients) provide about 1-3% of the total calories in the nutritional product.

One of the nutritional advantages of the lactalbumin hydrolysate in the protein system is that it provides some peptides to the patient. Evidence supports the existence of separate and noncompeting, carrier-mediated transport systems for free amino acids and for small peptides in the gastrointestinal tract. Uptake of peptides by the small intestine is nutritionally significant. Studies indicate that peptides are absorbed more rapidly than free-form amino acids. The physiologic importance of these separate transport systems is probably accentuated during malnutrition and other pathologic conditions because amino acid uptake from peptides is affected less than uptake of free amino acids.

Whey proteins such as lactalbumin have a high biologic value and contain an adequate supply of sulfur amino acids. Lactalbumin proteins have been reported to produce unique effects. For example, diets containing lactalbumin produced an enhanced immune response in mice. In a published report a comparison to mice fed a control diet, those fed lactalbumin showed significant increases in immunologic response to antigen, thymic weight, and cellularity and level of a complement protein. Partially hydrolyzed lactalbumin may be absorbed better and promote weight gain more effectively than either intact protein or free amino acids.

Arginine can have several physiologic effects. For example, accelerated wound healing and nitrogen retention after injury have been attributed to the feeding of arginine. The effects on wound healing may be due to increased synthesis of collagen in wounds. Published reports have indicated that rats fed diets supplemented with both arginine (2.4%) and glycine (1%) deposited more hydroxyproline (a component of collagen) in wounds that were healing when compared to animals fed control diets. Published studies have examined the effects of dietary arginine on cells of the immune system, such as T-lymphocytes and natural killer cells. Supplemental arginine may enhance immune function through increases in thymic weight and enhanced thymocyte and peripheral blood lymphocyte response to mitogens. Similarly, published reports have indicated that surgical patients whose diets were supplemented with arginine (25 g/day) exhibited increased T-lymphocyte activation compared with a group fed glycine. Another published study found that dietary L-arginine was important for lymphokine-activated killer cell activity. Other published studies have reported that diets providing 6% of total calories as arginine HCL were associated with an increased mortality in animal models of sepsis. The product of the present invention has 1-3% of the total calories provided by L-arginine.

The amino acid profile of the nutritional product of the present invention is presented in Table 3, and meets the standard for high biological protein set by the U.S. RDA Committee.

TABLE 3

| AMINO ACID | TARGET | g/100 g protein PREFERRED RANGE |
|---|---|---|
| INDISPENSABLE | | |
| Histidine | 2.1 | 1.7–2.4 |
| Isoleucine | 4.2 | 4.1–5.1 |
| Leucine | 9.0 | 7.9–12.5 |
| Lysine | 7.1 | 5.5–9.4 |
| Methionine | 2.3 | 2.1–2.9 |
| Phenylalanine | 4.1 | 3.5–4.9 |
| Threonine | 4.0 | 3.9–5.3 |
| Tryptophan | 1.2 | 1.1–2.0 |
| Valine | 5.0 | 4.8–6.5 |
| DISPENSABLE | | |
| Alanine | 3.3 | 2.9–4.4 |
| Arginine (Includes inherent arginine) | 12.1 | 9.0–14.0 |
| Aspartic Acid | 7.5 | 6.5–10.00 |
| Cystine | 1.1 | 0.7–2.2 |
| Glutamic Acid | 18.3 | 17.5–20.5 |
| Glycine | 1.6 | 1.5–1.9 |
| Proline | 8.0 | 6.5–9.0 |
| Serine | 4.9 | 4.8–5.1 |
| Tyrosine | 4.2 | 3.7–5.1 |

Carbohydrate is an important energy source for the injured individual as it is readily absorbed and utilized. It is the preferred fuel for the brain and red blood cells. The hyperglycemia of trauma is attributed to alterations in the hormonal milieu. This causes an increased rate of gluconeogenesis in the presence of elevated glucocorticoid, catecholamine, insulin and a hyperglycemic state. The carbohydrate in the product of the present invention is preferably provided primarily by hydrolyzed corn starch. A commercially available hydrolyzed corn starch commodity is Maltrin 100 which is distributed by Grain Processing Corporation of Muscatine, Iowa, U.S.A.

Although the formulation presented in Table 1 does not contain dietary fiber, it is considered to be within the scope of the present invention to employ dietary fiber in the nutritional product disclosed herein. Numerous types of dietary fibers are currently available. Basically, dietary fiber passes through the small intestine undigested by enzymes and is a kind of present invention to employ dietary fiber in the nutritional product disclosed herein. Numerous types of dietary fibers are currently available. Basically, dietary fiber passes through the small intestine undigested by enzymes and is a kind of natural and necessary laxative. As used herein and in the claims, dietary fiber is understood to be all of the components of food that are not broken down by enzymes in the human digestive tract to produce small molecular compounds which are then absorbed into the bloodstream. A nutritional product according to the invention has been made containing gum arabic or a source of dietary fiber. Another possible fiber sources that may be employed in the product is the blend of dieta fibers which is taught in commonly assigned U.S. Pat. No. 5,085,883.

Lipids provide energy and essential fatty acids and enhance absorption of the fat soluble vitamins. The type of lipid consumed affects many physiological parameters such as plasma lipid profile, membrane lipid composition and synthesis of mediators of the immune response such as prostaglandins and thromboxanes. Fat may be an appropriate fuel source for the hyperglycemic patient if peripheral tissues are insulin insensitive. The lipid system in the product of the present invention preferably comprises canola oil, medium chain triglycerides (fractionated coconut oil) and corn oil. Canola oil provides alpha linolenic acid, linoleic acid and oleic acid. It is relatively low in saturated fat. The omega three fatty acid provided by canola oil may have beneficial effects on the immune system, mediated through changes in the synthesis of prostaglandin. Corn oil is a source of Linoleic acid which is an essential fatty acid. Medium chain triglycerides are a readily absorbed source of energy and are useful in meeting the caloric need of stressed patients.

In a nutritional product according to the embodiment set forth in Table 1 the lipid system comprises by weight: (a) about 35–55%, preferably about 35–45%, and most preferably about 38–42% canola oil; (b) about 30–50%, preferably about 35–45%, and most preferably about 38–42% medium chain triglycerides (fractionated coconut oil; and (c) about 5–35%, preferably about 10–30%, most preferably about 15–25% corn oil. It is believed, however, that a satisfactory nutritional product according to the present invention may be made having a lipid system comprising about 40% medium chain triglycerides and about 60% canola oil. The lipid system provides a ratio of linoleic to alpha linolenic acid in the range of about 3.5:1 to about 5.5:1. The nutritional product of the present invention has about 4–5% of the total calories provided by the essential fatty acid linoleic acid. It has been recommended in the prior art that critically ill patients be provided with this level of linoleic acid. Preferably the fatty acid profile provided to the nutritional product is that set forth in Table 4.

TABLE 4

| FATTY ACID | TARGET | % Total Fatty Acids PREFERRED RANGE |
|---|---|---|
| ESSENTIAL | | |
| Linoleic (18:2ω6) | 21 | 19–24 |
| α-Linolenic (18:3ω3) | 4.5 | 3.5–12 |
| NONESSENTIAL | | |
| Caprylic (8:0) | 23 | 18–26 |
| Capric (10:0) | 10.3 | 10.2–15.5 |
| Lauric (12:0) | 0.1 | trace–0.4 |
| Myristic (14:0) | 0.3 | trace–0.7 |
| Palmitic (16:0) | 5.0 | 4.0–7.2 |
| Stearic (18:0) | 1.7 | trace–1.9 |
| Oleic (18:1ω9) | 31 | 20–45 |
| Arachidic (20:0) | 0.4 | trace–0.6 |
| Eiosenoic (20:1ω9) | 0.4 | trace–0.6 |
| Others | 2.3 | trace–10 |

There is evidence that vitamin A may reverse some of the immunosuppression which occurs following thermal injury or radiation injury; therefore, additional vitamin A for trauma patients may be beneficial. In particular, the cellular immune system may be responsive to vitamin A as measured by enhanced mixed lymphocyte reactions in burned animals given supplemental vitamin A palmitate. One published study examined the effects of vitamin A on impaired wound healing which accompanies radiation. Supplemental vitamin A administered prior to or after radiation or injury prevented the impaired wound healing, gastric ulceration and thymic involution which is typically observed. Beta carotene does not have the toxicity problems of vitamin A and may be the preferred form to add supplemental retinol equivalents to the diet. Beta carotene itself may enhance immune system function and functions as an antioxidant. The nutritional product of the present invention contains both vitamin A and beta carotene.

Vitamin E acts as an antioxidant and plays a role in the immune system, and is present in the nutritional product at a level of at least 45 IU per 1,500 kcals.

Taurine (β-aminoethanesulfonic acid) is involved in a wide variety of metabolic processes, including those of the central nervous system. It is involved in the conjugation of bile acids, helps regulate the aggregation of platelets, and aids in the function of neutrophils. Synthesized via cysteine, taurine is classified as a sulfur-containing amino acid. It is considered nonessential for humans under normal physiologic circumstances, although a decline in serum taurine concentrations suggests that taurine supplementation is needed in the post-injury state. A published study of severely burned patients indicated that the metabolism of methionine and cysteine may be altered after injury.

Carnitine is required metabolically to transfer long-chain fatty acids into the mitochondria for energy production. Carnitine is present in food, including meats and dairy products, and typical mixed diets provide 0.18 to 319 mg of carnitine/day. Published clinical trials have indicated that the excretion of carnitine increases after injury, and carnitine deficiency during antibiotic therapy has been reported. These results indicate that the supply of carnitine may be limited under certain circumstances and, therefore, should be supplied to trauma and major surgery patients.

Both taurine and carnitine are provided in a preferred embodiment of the present invention. The recommended intake of zinc is 15 mg/day for a healthy adult, and inadequate zinc intake by "healthy" people is not uncommon. An inadequate intake of zinc is associated with skin lesions, poor wound healing and immunodeficiency characterized by thymic atrophy. Alterations in zinc metabolism occur after trauma. For example, sepsis is associated with a decreased serum zinc level and an accumulation of zinc within the liver. The product of the present invention provides at least 100% of the U.S. RDA of zinc. The product of the invention contains vitamin C and the B vitamins in amounts greater than the U.S. RDA for an amount of product sufficient to provide 1500 kcal to insure adequate for hypermetabolic patients.

The nutritional product of the present invention has a moderate osmolality of about 425 Mosm/ky water, even though the product contains partially hydrolyzed proteins and has a greater caloric density as compared to prior art formulations. Formulations high in osmolarity may increase the risk of osmotic diarrhea. The nutritional product of the present invention has a viscosity of not greater than 55 cps, preferably about 25-45 cps, which is consistent with good tube feeding characteristics. The nutritional product of the present invention is intended primarily to be fed to a patient via a feeding tube in a manner which is well known in the art. However, it is considered to be within the scope of thes invention to add a flavoring system to allow oral feeding.

While the invention has been described with reference to the accompanying examples, it will be apparent to those skilled in the art that changes can be made without departing form the spirit or scope of the invention.

We claim:

1. A liquid nutritional product comprising: a protein system comprising by weight about 20-30% lactalbumin hydrolysate, about 60-70% partially hydrolyzed sodium caseinate, and about 8-14% L-arginine, supplemental L-arginine providing about 1-3% of the total calories in the nutritional product; and a lipid system having a ratio of linoleic acid to alpha linoleic acid in the range of about 3.5:1 to about 5.5:1, said nutritional product having a caloric density in the range of about 1.2 to 1.5 kcal/ml and a calorie to nitrogen ratio of about 112:1 to about 145:1.

2. A liquid nutritional product according to claim 1 wherein the nutritional product has a caloric density of about 1.3 kcal/ml.

3. A liquid nutritional product according to claim 1 wherein about 18-24% of the calories are provided by protein, about 20-30% of the calories are provided by lipids, and about 46-62% of the calories are provided by carbohyd-rates.

4. A liquid nutritional product according to claim 2 wherein about 18-24% of the calories are provided by protein, about 20-30% of the calories are provided by lipids, and about 46-62% of the calories are provided by carbohydrates.

5. A liquid nutritional product according to claim 1 wherein the lipid system comprises by weight about 35-55% canola oil, about 30-50% medium chai-n triglycerides and about 5-35% corn oil.

6. A liquid nutritional product according to claim 2 wherein the lipid system comprises by weight about 35-55% canola oil, about 30-50% medium chain triglycerides and about 5-35% corn oil.

7. A liquid nutritional product according to claim 3 wherein the lipid system comprises by weight about 35-55% canola oil, about 30-50% medium chain triglycerides and about 5-35% corn oil.

8. A liquid nutritional product according to claim 4 wherein the lipid system comprises by weight about 35-55% canola oil, about 30-50% medium chain triglycerides and about 5-35% corn oil.

9. A liquid nutritional product according to any one of claims 1-8 further comprising hydrolyzed corn starch as a carbohydrate source.

10. A liquid nutritional product comprising:
(a) a protein system which provides about 18-24% of the calories provided by the product, said protein system including (i) partially hydrolyzed protein and (ii) supplemental L-arginine in an amount sufficient to provide about 1-3% of the total calories provided by the product;
(b) a lipid system which provides about 20-30% of the calories provided by the product, said lipid system having a ratio of linoleic acid to alpha linoleic acid in the range of about 3.5:1 to about 5.5:1; and
(c) carbohydrates which provide about 46-62% of the calories provided by the product, the product having a caloric density in the range of about 1.2 to 1.5 kcal/ml a calorie to nitrogen ratio of about 112:1 to about 145:1, and having the following amino acid profile:

| AMINO ACID | g/100 g protein |
| --- | --- |
| Histidine | 1.7-2.4 |
| Isoleucine | 4.1-5.1 |
| Leucine | 7.9-12.5 |
| Lysine | 5.5-9.4 |

-continued

| AMINO ACID | g/100 g protein |
|---|---|
| Methionine | 2.1-2.9 |
| Phenylalanine | 3.5-4.9 |
| Threonine | 3.9-5.3 |
| Tryptophan | 1.1-2.0 |
| Valine | 4.8-6.5 |
| Alanine | 2.9-4.4 |
| Arginine (Includes inherent arginine) | 9.0-14.5 |
| Aspartic Acid | 6.5-10.00 |
| Cystine | 0.7-2.2 |
| Glutamic Acid | 17.5-20.5 |
| Glycine | 1.5-1.9 |
| Proline | 6.5-9.0 |
| Serine | 4.8-5.1 |
| Tyrosine | 3.7-5.1. |

11. A liquid nutritional product according to claim 10 wherein said product has the following fatty acid profile:

| FATTY ACID | % Total Fatty Acids |
|---|---|
| Linoleic (18:2ω6) | 19-24 |
| α-Linolenic (18:3ω3) | 3.5-12 |
| Caprylic (8:0) | 18-26 |
| Capric (10:0) | 10.2-15.5 |
| Lauric (12:0) | trace-0.4 |
| Myristic (14:0) | trace-0.7 |
| Palmitic (16:0) | 4.0-7.2 |
| Stearic (18:0) | trace-1.9 |
| Oleic (18:1ω9) | 20-55 |
| Arachidic (20:0) | trace-0.6 |
| Eiosenoic (20:1ω9) | trace-0.6 |
| Others | trace-10. |

12. A liquid nutritional product according to claim 10 wherein the product has a caloric density of about 1.3 kcal/ml.

13. A liquid nutritional product according to claim 11 wherein the product has a caloric density of about 1.3 kcal/ml.

14. A liquid nutritional product according to claims 10 wherein the product has viscosity of not greater than 55 cps.

15. A liquid nutritional product according to claim 11 wherein the product has a viscosity of not greater than 55 cps.

16. A liquid nutritional product according to claim 12 wherein the product has a viscosity of not greater than 55 cps.

17. A liquid nutritional product according to claim 13 wherein the product has a viscosity of not greater than 55 cps.

18. A liquid nutritional product according to one of claims 10-17 further comprising a source of dietary fiber.

19. A liquid nutritional product comprising
(a) a protein system comprising by weight about 20-30% lactalbumin hydrolysate, about 62-68% partially hydrolyzed sodium caseinate, and about 8-12% L-arginine, supplemental L-arginine providing about 1-3% of the total calories in the nutritional product;
(b) a lipid system comprising by weight about 35-45% canola oil, about 35-45% medium chain triglycerides, and about 10-30% corn oil, the lipid system providing a ratio of linoleic acid to alpha linoleic acid in the range of about 3.5:1 to about 5.5:1; and
(c) a carbohydrate system comprising hydrolyzed corn starch, the nutritional product having (i) a caloric density of about 1.3 kcal/ml, (ii) a caloric distribution such that about 18-24% of the calories are provided by proteins, about 20-30% of the calories are provided by lipids and about 46-62% of the calories are provided by carbohydrates, (iii) the nutritional product has a viscosity of not greater than 55 cps, and (iv) a calorie to nitrogen ratio of about 112:1 to about 145:1.

20. A liquid nutritional product according to claim 19 further comprising carrageenan.

21. A liquid nutritional product according to claim 20 wherein a quantity of said product sufficient to provide 1,500 kcal will provide at least 100% of the U.S. RDA of Vitamin A, Vitamin D, Vitamin E, Vitamin K, Vitamin C, Folic Acid, Thiamin, Riboflavin, Vitamin B-6, Vitamin B-12, Niacin, Biotin, Pantothenic Acid, Calcium, Phosphorus, Magnesium, Iodine, Copper, Zinc and Iron.

22. A liquid nutritional product according to claim 21 wherein a quantity of said product sufficient to provide 1,500 kcal will provide at least 100% of the U.S. RDA of Vitamin A, Vitamin D, Vitamin E, Vitamin K, Vitamin C, Folic Acid, Thiamin, Riboflavin, Vitamin B-6, Vitamin B-12, Niacin, Biotin, Pantothenic Acid, Calcium, Phosphorus, Magnesium, Iodine, Copper, Zinc and Iron.

23. A liquid nutritional product according to claim 20 further comprising beta carotene.

24. A liquid nutritional product according to claim 21 further comprising beta carotene.

25. A liquid nutritional product aoccording to claim 22 further comprising beta carotene.

26. A liquid nutritional product according to claim 23 further comprising beta carotene.

* * * * *

UNITED STATES PATENT AND TRADEMARK OFFICE
CERTIFICATE OF CORRECTION

PATENT NO. : 5,221,668
DATED : June 22, 1993
INVENTOR(S) : Mary F. Henningfield, et. al.

It is certified that error appears in the above-indentified patent and that said Letters Patent is hereby corrected as shown below:

Column 2, line 19, "ofmalnutrition" should be -- of malnutrition--.
Column 2, line 19, "thelevel" should be --the level--.
Column 6, line 31, "solution remaining" should be --solution. The remaining--.
Column 11, line 61, "dieta" should be --dietary--
Column 14, line 19, "carbohyd-rates" should be --carbohydrates--.
Column 14, line 27, "chai-n" should be --chain--.

Signed and Sealed this

Nineteenth Day of July, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO.     : 5,221,668
DATED          : June 22, 1993
INVENTOR(S)    : Henningfield et al.

Page 1 of 1

It is certified that error appears in the above-identified patent and that said Letters Patent is hereby corrected as shown below:

Column 14,
Line 7, "alpha linoleic" should read -- alpha linolenic-acid --
Line 54, "alpha linoleic" should read -- alpha linolenic-acid --

Signed and Sealed this

Eighth Day of April, 2003

JAMES E. ROGAN
*Director of the United States Patent and Trademark Office*